United States Patent [19]

Engel et al.

[11] Patent Number: 4,542,159

[45] Date of Patent: Sep. 17, 1985

[54] CYCLOALIPHATIC KETOAMINES

[75] Inventors: Jürgen Engel, Alzenau; Axel Kleemann, Hanau; Klaus Posselt, Bonn; Fritz Stroman, Offenbach; Klaus Thiemer, Hanau, all of Fed. Rep. of Germany

[73] Assignee: Degussa Akteinsellschaft, Frankfurt, Fed. Rep. of Germany

[21] Appl. No.: 39,436

[22] Filed: May 15, 1979

[30] Foreign Application Priority Data

May 17, 1978 [GB] United Kingdom ............... 20049/78

[51] Int. Cl.⁴ .................... A61K 31/135; C07C 91/23; C07C 91/34; C07C 97/10
[52] U.S. Cl. .............................. 514/653; 260/455 B; 260/456 A; 260/463; 260/465 B; 260/544 N; 514/929; 560/39; 560/86; 560/138; 560/142; 562/444; 564/302; 564/304; 564/364
[58] Field of Search .................... 424/330; 260/570.6; 564/364, 365, 363

[56] References Cited

U.S. PATENT DOCUMENTS

| | | | |
|---|---|---|---|
| 3,395,143 | 7/1968 | Thiele et al. | 260/570.6 |
| 3,646,145 | 2/1972 | Thiele | 260/570.6 |
| 3,829,469 | 8/1974 | Thiele et al. | 260/570.6 |
| 4,131,686 | 12/1978 | Ikezaki et al. | 260/570.6 |

FOREIGN PATENT DOCUMENTS

| | | |
|---|---|---|
| 1212542 | 3/1966 | Fed. Rep. of Germany. |
| 1493574 | 4/1971 | Fed. Rep. of Germany. |
| 2085683 | 12/1971 | France. |
| 2266496 | 10/1975 | France. |
| 1094461 | 12/1967 | United Kingdom. |

OTHER PUBLICATIONS

Kalm J. Org. Chem. vol. 25, pp. 1929-1937.
Pfanz, Liebigs Annalen, vol. 614, pp. 149-158.
Royals, J. Org. Chem., vol. 15, pp. 1147-1154.

*Primary Examiner*—Vivian Garner
*Attorney, Agent, or Firm*—Cushman, Darby & Cushman

[57] ABSTRACT

There are prepared compounds of the formula:

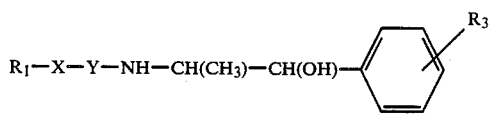

wherein X is the group $>C=O$ or $>CH(OH)$, Y is the group

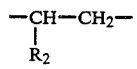

$R_2$ is hydrogen or $C_1$ to $C_6$ alkyl, $R_3$ is hydrogen or a hydroxy group and $R_1$ is the adamantyl group or a saturated or single unsaturated $C_3$ to $C_{16}$ cycloalkyl group where the $C_3$ to $C_{16}$ cycloalkyl group can be substituted by a $C_1$-$C_4$ alkyl group or a halogen atom and their salts. The compounds are useful in dilating the peripheral blood vessels and in lowering blood pressure.

19 Claims, No Drawings

CYCLOALIPHATIC KETOAMINES

BACKGROUND OF THE INVENTION

There are known compounds of the general formula

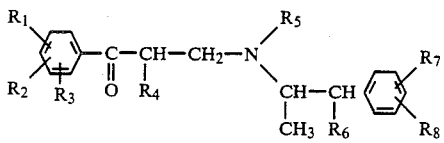

from German Pat. No. 1,493,574. In this formula $R_1$, $R_2$ and $R_3$ are the same or different and are hydrogen or a hydroxy group, a methoxy group or chlorine. $R_4$ is hydrogen or a methyl or ethyl group. $R_5$ is hydrogen or a methyl group. $R_6$ is hydrogen or a hydroxy group. $R_7$ and $R_8$ are the same or different and are a methyl group, a methoxy group or chlorine.

These compounds are pharmacodynamically active and particularly improve the heart function.

SUMMARY OF THE INVENTION

The invention is directed to new compounds of the formula

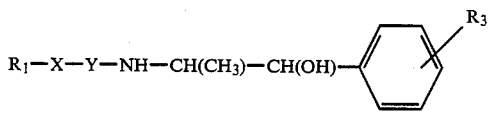

where X is the group $>CO$ or $>CH(OH)$, Y is

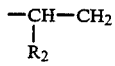

$R_2$ is hydrogen or a $C_1$ to $C_6$ alkyl group and $R_3$ is hydrogen or a hydroxy group and $R_1$ is the adamantyl group or a saturated or single unsaturated $C_3$ to $C_{16}$ cycloalkyl group wherein the $C_3$ to $C_{16}$ cycloalkyl group can also be substituted by a $C_1$ to $C_4$ alkyl group or a halogen atom, e.g. fluorine, bromine, chlorine or iodine, and their salts, e.g., salts with a pharmaceutically acceptable acid.

$R_2$ is preferably a $C_1$ to $C_4$ alkyl group, especially methyl or ethyl. The saturated or unsaturated $C_3$ to $C_{16}$ cycloalkyl group preferably has 3 to 12 carbon atoms, particularly 3 to 8 carbon atoms. In the case where the cycloalkyl group is substituted then it is preferably substituted once or twice with the same or different substituents such as methyl, ethyl, chlorine, bromine and/or fluorine.

The compounds of the invention are pharmacodynamically active and for example cause a lowering of the blood pressure as well as an improvement of the cerebral or peripheral blood flow. Besides they possess an antiphlogistic action and are distinguished by a good resorption. For example in intraduodenal application (narcotized dog) there is obtained after 15 minutes the maximum of the biological effect (for example in the improvement of the femoralis blood flow). The distinguished resorption also is shown through the biological effect which occurs (for example increase of the blood flow in the Arteria Femoralis) at equal dosage being nearly identical in intraduodenal application and in intravenous application.

In addition to the compounds mentioned in the specific examples there are also included within the invention for example 1-[3-hydroxy-3-phenyl-propyl-(2)]-(2-ethyl-3-cyclohexyl-3-oxo-propyl)-amine, 1-[3-hydroxyphenyl-propyl(2)]-(2-ethyl-3-cyclohexyl-3-hydroxy-propyl)-amine, 1-[3-hydroxy-3-phenyl-propyl-(2)]-(2-butyl-3-cyclohexyl-3-oxo-propyl)-amine, 1-[3-hydroxy-3-phenylpropyl-(2)]-(2-hexyl-3-cyclohexyl-3-oxo-propyl)-amine, 1-[3-hydroxy-3-phenyl-propyl-(2)]-(3-cyclohexadecyl-3-oxo-propyl)-amine, 1-[3-hydroxy-3-phenyl-propyl-(2)]-[3-(1-cyclohexadecen-1-yl)-3-oxo-propyl]-amine, 1-[3-hydroxy-3-(4-hydroxyphenyl)-propyl-(2)]-[3-(2-bromocyclopenten-1-yl)-3-oxo-propyl]-amine, 1-[3-hydroxy-3-phenylpropyl-(2)]-[3-(2-chlorocyclohexyl)-3-oxo-propyl]-amine, 1-[3-hydroxy-3-phenyl-propyl-(2)]-[3-(2-fluorocyclohexyl)-3-oxo-propyl]-amine, 1-[3-hydroxy-3-phenyl-propyl-(2)]-[3-(2-methyl-3-chlorocyclohexyl)-3-oxo-propyl]-amine, 1-[3-hydroxy-3-phenyl-propyl-(2)]-[3-(2,4-dimethyl cyclohexyl)-3-oxo-propyl-(2)]-amine, 1-[3-hydroxy-3-phenylpropyl-(2)]-[3-(3-ethyl-1-cyclohexen-1-yl)-3-oxo-propyl]-amine, 1-[3-hydroxy-3-phenyl-propyl-(2)]-[3-(3-butyl-1-cyclohexen-1-yl)-3-oxo-propyl]-amine, 1-[3-hydroxy-3-phenyl-propyl-(2)]-[3-(1-cycloundecyl)-3-oxo-propyl]-amine, 1-[3-hydroxy-3-phenyl-propyl-(2)]-[3-(2-methylcyclohexyl)-3-oxo-propyl]-amine, 1-[3-hydroxy-3-phenyl-propyl-(2)]-[3-(2-ethylcyclohexyl)-3-oxo-propyl]-amine, and 1-[3-hydroxy-3-phenyl-propyl-(2)]-[3-(4-butylcyclohexyl)-3-oxo-propyl]-amine.

In the stated processes for production of the compounds it is frequently suitable to protect the phenolic hydroxyl group in the starting materials by a protective group known as of itself. Frequently such protective groups are already needed for the production of the starting compounds themselves. These protective groups are easily split off from the end products. It is either a matter of readily solvolytically cleavable acyl groups, (e.g. the acetyl group) or hydrogenatingly cleavable groups, as for example the benzyl group. The solvolytically cleavable protective groups are split off for example by saponification with dilute mineral acids, e.g., hydrochloric acid, in a solution or suspension (lower alcohols, e.g., ethanol) at a temperature between 10° and 150° C. Depending on the type of protective groups, however, there can also take place cleavage during the reaction process. The latter is the case for example if the phenolic hydroxy group is protected by a benzyl group or the carbobenzoxy group and the process includes a hydrogenation step. If the protective group is not split off during the reaction then there is needed a simple subsequent treatment of the reaction product as a result of which the cleavage of the protective group then takes place, for example under conditions such as those given above.

As protective groups there can be used for example: benzyl groups, α-phenylethyl groups, benzyl groups substituted in the benzene nucleus, as for example the p-bromo or p-nitro benzyl group, the carbobenzoxy groups, the carbobenzthio group, the trifluoroacetyl group, the phthalyl group, the trityl group, the p-toluenesulfonyl group and the like, as well as additionally simple acyl groups as for example alkanoyl groups such as the acetyl group, formyl group or the tert. butyl carboxy group.

The reduction of the keto group of compounds wherein X is the group $>CO$ to compounds where X is the group >CHOH, as well as the reduction of a double bond of the group $R_1$ is generally carried out by catalytic hydrogenation. As catalysts there can be used for example the customary finely divided metal catalysts such as noble metal catalysts as for example Raney-nickel, platinum or particularly palladium. The process can be carried out at normal temperature. Suitably there is used a temperature range of about 40° to 200° C., in a given case under elevated pressure (1-100, especially 1-50 bar). If the phenolic hydroxyl group contains the benzyl protective group then this is simultaneously split off in the catalytic hydrogenation, if for example palladium catalyst is used.

The reduction of the keto group, however, is likewise possible in a different way, for example by means of complex metal hydrides (for example lithium aluminum hydride, sodium borohydride, cyanoborohydride, lithium-tri-tert.butoxy aluminium hydride) or by means of aluminum alcoholates according to Meerwein and Ponndorf (for example by means of aluminum isopropylate) at a temperature between 0° and 150° C., especially 20° to 100° C. As solvents or suspension agents for this reaction there can be considered for example, lower aliphatic alcohols (e.g. ethanol), dioxane, tetrahydrofurane, water or aromatic hydrocarbons such as benzene or toluene as well as mixtures of these agents.

A selective reduction of a double bond of the group $R_1$ for example is possible under careful conditions by hydrogenation in the presence of noble metal catalysts (Pd, Pt) or Raney nickel.

The production of the compounds of the invention takes place according to the process which is defined, for example in the process claims.

The compounds of formula I

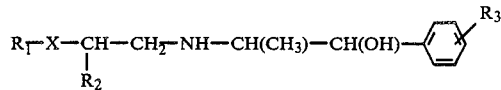

can be produced either by (a) reacting an amine of general formula

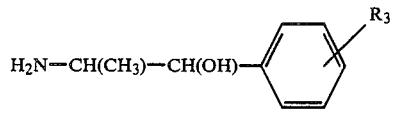

where $R_3$ is as defined above with a compound of the general formula

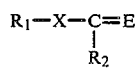

where X, $R_1$ and $R_2$ are as defined above and E is a methylene group or a hydrogen atom and the group $-CH_2-NRaRb$ where Ra and Rb are lower alkyl groups or NRaRb is closed to form a ring or E is two hydrogen atoms, if X is the CO group and in the presence of formaldehyde or a formaldehyde liberating material or (b) reacting a compound of the general formula

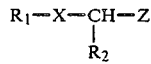

where $R_1$, $R_2$ and X are as defined above and Z is a halomethyl group (e.g., chloromethyl or bromomethyl), an aminomethyl group or a formyl group with a compound of the general formula

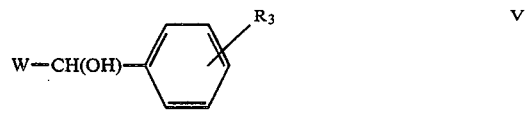

where $R_3$ is a defined above and W is a 1-haloethyl group (e.g. 1-chloroethyl or 1-bromoethyl), a 1-aminoethyl group or a 1-oxo-ethyl group or together with the hydroxyl group also forms an epoxy ring and wherein Z and W are always different from each other and in the presence of hydrogen, in the case an oxo group is present, wherein the latter case in the starting compound V the secondary hydroxy group can be replaced by an oxo group or (c) reacting a compound of the general formula

where $R_1$ is as defined above and M indicates lithium, $-MgCl$, $-MgBr$ or $-MgI$ with a compound of the general formula

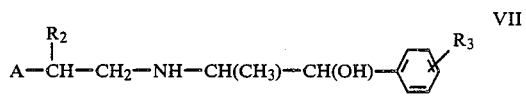

where $R_2$ and $R_3$ are as defined above and A is a carboxy group, a $C_1$ to $C_5$ carbalkoxy group, a halocarbonyl group or a cyano group and in compounds of formula I obtained according to the stated process wherein $R_1$ contains a double bond and/or X is the CO group, in a given case reducing this double bond and/or this CO group.

PROCESS (a)

This process is generally carried out in an inert solvent or suspension medium at a temperature between 5° and 250° C. As solvents there can be used for example, lower aliphatic alcohols (e.g. ethanol, methanol, propanol, isopropanol), saturated alicyclic and cyclic ethers (e.g., dioxane, tetrahydrofuran, diethyl ether), lower aliphatic ketones (e.g. acetone), lower aliphatic hydrocarbons or halohydrocarbons (e.g., chloroform, 1,2-dichloroethane, hexane, petroleum ether), aromatic hydrocarbons, (e.g., benzene, xylene, toluene), glacial acetic acid, water or mixtures of these materials. In the case where there is used as the starting material a compound of formula III wherein E is the group >CH$_2$ the work is carried out for the most part in the lower portion of the stated temperature range (5° to 80° C.), whereby there are in this case particularly considered as solvents lower alcohols, ether, acetone, dioxane or chloroform. In using a compound III wherein E is hydrogen and the group $-CH_2-NRaRb$ the work is carried out for the most part in a higher temperature range (80° to 250° C.,) especially 80° to 150° C. in case X=CO), whereby there are used as solvents particularly water, alcohol-water or a two phase system such as water-benzene or water-toluene.

In the case where there is used a starting material of formula III where E is two hydrogen atoms the operation is carried out especially between 20° and 150° C.

As formaldehyde yielding materials for example there can be employed formaldehyde acetals from which formaldehyde is set free in the presence of acid anions, as for example polyformaldehyde, paraformaldehyde, hexamethylenetetramine. In place of formaldehyde and the amine of formula II there can also be reacted an oxazolidine of the formula

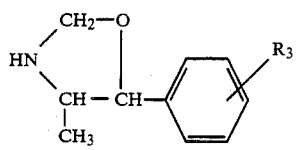

previously produced from these materials or there can be used a mineral acid addition salt (for example hydrochloride, hydrobromide) of such an oxazolidine with the compound of formula $R_1$—CO—$C(R_2)H_2$. In case the oxazolidine derivative is not added as a salt it is suitable to work in the presence of dilute mineral acids (for example 20% alcoholic hydrochloric acid or hydrobromic acid).

The production of the above mentioned oxazolidine is carried out according to Kalm, J. Org. Chemistry Vol. 25, pages 1929-1937 (1960) or Pfanz, Leibigs Ann. Vol. 614, pages 149-158 (1958).

The starting materials of the formula $R_1$—CO—$C(R_2)H_2$ where $R_1$ is a saturated cycloalkyl group can be obtained for example from the corresponding unsaturated compounds (producible according to Royals, J. Org. Chem. Vol. 15, pages 1147-1154 (1950) by catalytic hydrogenation in the presence of metallic hydrogenation catalysts (Pd) in lower alcohols between 20° and 100° C.

Starting materials of the formula $R_1$—X—$C(R_2)H$—$CH_2$—$NR_aR_b$ can be obtained for example by Mannich reaction of ketones of the formula $R_1$—CO—$C(R_2)H_2$ with dimethylamine hydrochloride in the presence of formaldehyde. Starting materials of the formula $R_1$—X—$C(R_2)$=$CH_2$ can be obtained for example from ketones of the formula $R_1$—CO—$C(R_2)H$—$CH_2$—$NR_aR_b$ by splitting off of the amine portion (for exmample by steam distillation) or through thermal HCl splitting out from the corresponding cycloaliphatic β-chloroethyl-ketone of the formula $R_1$13 CO—CH($R_2$)—$CH_2Cl$. A double bond present in $R_1$ and/or the CO group X can then likewise in a given case be reduced (the >CO group to the >CH(OH) group.

PROCESS (b)

This process is suitably carried out in a solution or suspension medium such as aromatic hydrocarbons (benzene, toluene, xylene), aliphatic alcohols (ethanol, propanol, butanol), lower aliphatic carboxylic acid amides (dimethyl formamide), tetramethyl urea, dimethyl sulfoxide, acyclic and cyclic saturated ethers (diethyl ether, dioxane) at a temperature between 20° and 200° C., particularly 50° to 140° C. It is recommended to work in the presence of an acid acceptor, alkali carbonate, e.g., potassium carbonate or sodium carbonate, alkali, alcoholate, e.g., sodium ethylate, alkali amide, e.g., sodamide, tertiary amines, e.g., tributyl amine) in the case for example where Z contains a halogen atom and W is an amino group (or the reverse). As halogen atoms there are included for example chlorine, bromine and iodine. Excess amine can also serve as acid acceptor.

The process is carried out in the presence of hydrogen in the case where Z is an aminomethyl group and W is the 1-oxo-ethyl group or in the case where Z is a formyl group and W is the 1-amino-ethyl group.

As catalysts there can be employed the customary hydrogenation catalysts, preferably metallic hydrogenation catalysts such as Raney-nickel, platinum, palladium. However, there can also be used alkali borohydrides ($NaBH_4$).

If simultaneously with the hydrogenating condensation a benzyl protective group or another hydrogenatingly cleavable protective group is removed, then it is preferable to use palladium catalysts.

Frequently it is favorable to use an amine starting compound in which a hydrogen atom of the amino group is protected by a benzyl protective group (in place of the aminomethyl group or 1-amino-2-ethyl group Z or W then signifies for example a benzylaminomethyl group or a 1-benzylamino ethyl group. In this case there is preferably used palladium on carbon, palladium on barium sulfate, palladium on aluminum oxide).

Starting materials of the formula $R_1$—X—$C(R_2)H$—$CH_2$—Hal (Hal=halogen atom) can be obtained for example by conventional addition of hydrogen halide, e.g., hydrogen chloride, to the unsaturated compound $R_1$—X—$C(R_2)$=$CH_2$ or by known reaction of a compound $R_1H$ with β-chloropropionyl chloride in the presence of Friedel-Crafts catalysts, e.g. aluminum chloride, or also by acylation of ethylene or $CH(R_2)$=$CH_2$ with a compound $R_1COCl$ under Friedel-Crafts conditions and in a given case subsequently reducing the keto group.

A double bond or the CO- group X can then in a given case be reduced in the usual manner.

Starting materials of the formula $R_1$—X—$C(R_2)H$—CHO can be obtained for example by reaction of a Grignard compound or an alkali derivative of the compound $R_1H$ with a compound Hal—$C(R_2)H$—CH—$(OC_2H_5)_2$ analogous to the process given in German patent 1,212,542.

Starting materials of the formula $R_1$—X—$C(R_2)H$—$CH_2$—$NH_2$ can be obtained for example from the corresponding halogen compounds and potassium phthalimide in a solvent (toluene, xylene) at the boiling temperature and subsequent cleavage of the phthalimide residue by mineral acid (25% HCl) in a solution or suspension medium (glacial acetic acid/$H_2O$; alcohol/$H_2O$) between 80° and 200° C.

PROCESS (c)

This process is carried out in a solvent or suspension medium at a temperature between 0° and 150° C. As solvents for example there can be employed those customarily used for Grignard reaction as for example lower, aliphatic ether (diisobutyl ether), tetrahydrofurane, aromatic hydrocarbons (benzene, toluene, xylene).

Starting materials of formula VI can be obtained for example from compound $R_1$Hal (Hal=chlorine, bromine or iodine) and magnesium or lithium by customary Grignard reaction.

Starting materials of formula VII can be obtained by reaction of a compound of the formula

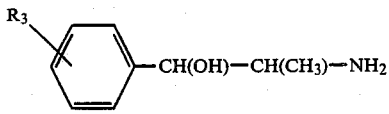

with an unsaturated compound of the formula

with or without solvent at a temperature between 20° and 100° C. (A is preferably -CN or carbalkoxy). As solvents there can be used for example lower alcohols, ether, dioxane, benzene. By saponification or customary reaction with a halogenating agent there is obtained therefrom such starting materials wherein A is the carbalkoxy group or halocarbonyl group.

Depending on the process conditions and starting materials there is obtained the final product, e.g. of formula I, as the free base or in the form of its salt. The salts of the final product can be converted in known manner, for example with alkali, e.g. sodium hydroxide or potassium hydroxide or ion exchangers, for example basic ion exchangers, again into the base. From the latter there are recovered salts by reaction with organic or inorganic acids, especially those which are suited to form therapeutically useful (e.g. pharmaceutically acceptable) salts. As such acids there can be mentioned for example: hydrohalic acids, e.g. hydrochloric acid and hydrobromic acid, sulfuric acid, phosphoric acid, phosphorous acid, nitric acid, perchloric acid, organic mono, di or tricarboxylic acids of the aliphatic, alicyclic, aromatic or heterocyclic series as well as sulfonic acids. Example of these are: formic acid, acetic acid, propionic acid, succinic acid, glycolic acid, lactic acid, adipic acid, tartaric acid, citric acid, ascorbic acid, maleic acid, fumaric acid, hydroxymaleic acid or pyruvic acid; phenyl acetic acid, benzoic acid, p-aminobenzoic acid, anthranilic acid, p-hydroxybenzoic acid, salicylic acid or p-aminosalicylic acid, embonic acid, methanesulfonic acid, ethanesulfonic acid, hydroxyethanesulfonic acid, ethylenesulfonic acid, halobenzene sulfonic acid, e.g. p-chlorobenzenesulfonic acid, benzenesulfonic acid, toluene sulfonic acid, e.g. p-toluenesulfonic acid, naphthalene sulfonic acid or sulfanilic acid or even 8-chlorotheophylline.

Those compound which contain asymmetric carbon atoms and as a rule occur as racemates can be split into the optically active isomers in known manner, for example by means of an optically active acid. However, it is also possible from the beginning to add optically active or also diastereomeric starting materials in which case there is then obtained as the final product a corresponding pure optically active form or diastereomer configuration. For example it is a matter of compounds of the norephedrine and the pseudo norephedrine configuration. There can also occur diastereomeric racemates, since in the compounds produced there are present two or more asymmetrical carbon atoms. Separation is possible in the usual manner, for example by recrystallization.

The compounds of the invention are suited for the production of pharmaceutical compositions. The pharmaceutical compositions or medicaments can contain one or more of the compounds of the invention or even mixtures of the same with other pharmaceutically active materials. For the production of pharmaceutical preparations there can be used the customary pharmaceutical carriers and assistants. The medicines can be employed internally, parenterally, orally or perlingually. For example dispensation can take place in the form of tablets, capsules, pills, dragees, plugs, salves, jellies, creams, powders, liquids, dusts or aerosols. As liquids there can be used for example oily or aqueous solutions or suspensions, emulsions, injectable aqueous and oily solutions or suspensions.

The compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared with the usual pharmaceutical excipients, assistants, carriers, and diluents.

As carriers and assistants, for example, are those recommended in the following literature as adjuvants for pharmacy, cosmetic and related fields such as in Ullmann's Encyklopädie der technischen Chemie, Vol. 4 (1953), pages 1 to 39; Journal of Pharmaceutical Sciences 52 (1963), pages 918 et seq.; H. v. Czetsch-Lindenwald, Hilfstoffe fur Pharmazie und angrenzende Gebiete; Phar. Ind. 2 (1961), pages 72 et seq.; Dr. H. P. Fielder, Lexicon der Hilftstoffe fur Pharmazie, Kosmetik und angrenzende Gebiete, Cantor Kg. Aulendorf i. Württ. (1971).

Examples of such materials include gelatin, natural sugars such as sucrose or lactose, lecithin, pectin, starch (for example cornstarch), alginic acid, tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols (for example methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example calcium stearate, calcium laurate, magnesium oleate, calcium palmitate, calcium behenate and magnesium stearate), emulsifiers, oils and fats, especially of plant origin (for example peanut oil, castor oil, olive oil, sesame oil, cottonseed oil, corn oil, wheat germ oil, sunflower seed oil, cod-liver oil), mono-, di- and triglycerides of saturated fatty acids ($C_{12}H_{24}O_2$ to $C_{18}H_{36}O_2$ and their mixtures, e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atoms alkanols) or polyhydric alcohols such as glycols, glycerine, diethylene glycol, pentaerythritol, sorbitol, mannitol, ethyl alcohol, butyl, alcohol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatiges, dimethyl sulfoxide, fatty alcohols, e.g., stearyl alcohol, cetyl alcohol, lauryl alcohol and oleyl alcohol, triglycerides, e.g., glyceryl olate, glyceryl stearate, glyceryl palmitate, and glyceryl acetate, partial esters of glycerine, e.g., monoacetic, diacetin, glyceryl monostearate, glyceryl distearate, glyceryl monopalmitate, paraffins and the like.

In the production of the preparation there can be used known and customary solution aids or emulsifiers. As solution aids and emulsifiers there can be used, for example, polyvinyl pyrrolidone, sorbitan fatty acid esters such as sorbitan trioleate, lecithin, gum acacia, gum tragacanth, polyoxyethylated sorbitan monoleate, polyoxyethylated fats, polyoxethylated oleotriglycerides, linolized oleotriglycerides, polyethylene oxide-condensation products of fatty alcohols, alkylphenols or fatty acids. As used herein polyoxyethylated means that the materials in question contain polyoxyethylene chains whose degree of polymerization generally is between 2 and 40, particularly between 10 and 20.

Such polyoxethylated materials for example can be obtained by reaction of hydroxyl group containing compounds (for example mono- or diglycerides) or unsaturated compounds such as, for example, those containing the oleic acid radical with ethylene oxide (for example 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191-195).

Furthermore, there can be added preservatives, stabilizers, buffers, for example, calcium hydrogen phosphate, colloidal aluminum hydroxide, taste correctives, antioxidants and complex formers (for example ethylene diamine tetracetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium metabisulfite, ascorbic acid, gallic acid, alkyl gallates, e.g., methyl gallate and ethyl gallate, butyl hydroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester), benzoic acid, sodium benzoate, trichloroisobutyl alcohol, phenol, cresol, benzethonium chloride and formalin, derivatives).

The pharmacological and galenical treatment of the compounds of the invention takes place according to the usual standard method. For example, the active material or materials and assistants or carriers are well mixed by stirring or homogenization (for example by means of a colloid mill or ball mill), wherein the operation is generally carried out at temperatures between 20° and 80° C., preferably 20° to 50° C.

The application of active material or drug can take place on the skin or mucous membrane or internally, for example, orally, enterally, pulmonally, rectally, intravenously, nasally, vaginally, lingually, intramuscularly, intraarterially, intracardially, intramuscularly, or intraperitoneally, subcutaneously or intracutaneously.

The addition of other medicines is also possible or favorable.

The compounds of the invention on the narcotized dog exhibit a strong and continuous widening of the peripheral blood vessels (measured with an electromagnetic flowmeter, see for example A. Kolin and R. T. Kada, Proc. Natl. Akad. Sc. 45, 1312 (1959) or Best-Taylor, The Physiological Basis of Medical Practice, Baltimore 1966, 8th edition, page 702, et seg.) with simultaneous increase of the cardiac activity measured on the heart time volumes. The heart time volumes were ascertained by the cold dilution method according to H. Slama and J. Püper, Kreislaufforschung Vol. 53, page 322 (1964).

For example with the above mentioned test method there is obtained at a dosage of 1.5 mg/kg of body weight of dog intraduodenally an increase of the blood flow in the arterial femoralis of about 40% (average over 180 minutes).

This blood vessel widening activity is comparable with the action of the known medicine cinnarizin.

The lowest, haemodynamically effective dosage in the above stated animal tests for example is 0.3 mg/kg orally, 0,03 mg/kg intravenously.

As the general dosage range for the blood vessel widening effect (animal experiments as above) there can be used for example:

1-20 mg/kg orally, especially 3 to 10 mg/kg or 0.1-5 mg/kg intravenously, especially 0.3 to 3 mg/kg.

The compounds of the invention are indicated for: peripheral blood flow disturbances, cerebral blood flow disturbances, acute glycoside refractory insufficiency, diabetic angiopathy, ulcus crunis, functional blood flow disturbances, stopping labor pains at threatening abortion.

The pharmaceutical preparations generally contain between 1 and 50 mg of the active component or components of the invention.

The compounds can be delivered in the form of tablets, capsules, pills, dragees, plugs, salves, gels creams, powders, dusts, aerosols or in liquid form. As liquid forms there can be used for example oily or alcoholic or aqueous solutions as well as suspensions and emulsions. The preferred forms of use are tablets which contain between 5 and 50 mg or solutions which contain between 0.1 and 10% of active material.

In individual doses the amount of active components of the invention can be used for example in an amount of:

a. in oral dispensation between 5 and 100 mg;

b. in parenteral dispensation (for example intravenously, intramuscularly) between 0.5 and 20 mg.

For example, there is recommended the use of 1 to 3 tablets containing 10zto 20 mg of active ingredient 3 times daily or for example, intravenously the injection 1 to 5 times daily of a 2 to 10 ml ampoule containing 5 to 15 mg of active substance. In oral dispensation the minimum daily dosage for example is 10 mg; the maximum daily dosage in oral administation should not be over 300 mg.

The dosages in each case are based on the free base.

The acute toxicity of the compounds of the invention in the mouse (expressed by the $LD_{50}$ mg/kg method of Miller and Tainter, Proc. Soc. Exper. Biol. and Med. 57 (1944), pages 261 et seq.) in oral application is between 250 mg/kg and 600 mg/kg.

The drugs can be used in human medicine, in veterinary medicine as well as in agriculture alone or in admixture with other pharmacologically active materials. The compounds can be used to treat dogs, cats, horses and cattle.

The compositions can comprise, consist essentially of or consist of the materials set forth.

In the treatment of dogs and cats the individual oral dosages are generally between about 0.3 and 5 mg/kg of body weight; the parenteral dosage between about 0.1 and 10 mg/kg body weight.

In the treatment of horses and cattle the individual oral dosages are generally between 0.3 and 5 mg/kg body weight; the parenteral dosages between about 0.1 and 10 mg/kg body weight.

The methods can comprise, consist essentially of or consist of the steps set forth with materials shown. The compositions can comprise, consist essentially of or consist of the materials set forth.

Unless otherwise indicated all parts and percentages are by weight.

In the following example the yields are always based on the norephedrine or hydroxynorephedrine employed.

The corresponding d-isomer or the racemate are obtained if for example in place of the left turning norephedrine starting compound there is used the corresponding right turning form or the racemate.

Frequently it is recommended in order to isolate the reaction products which for the most part are formed directly as the hydrochloride to convert them into the free base, for example by treating with dilute ammonia and in a given case this again to convert into a salt in conventional manner.

DESCRIPTION OF THE PREFERRED EMBODIMENTS

EXAMPLE 1

1-[3-Hydroxy-3-phenyl-propyl-(2)]-[3-(1-cyclohexen-1-yl)-3-oxo-propyl]-amine

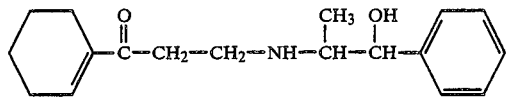

74.5 grams (0.6 mol) of 1-acetyl-1-cyclohexene, 93.8 grams (0.5 mol) of 1-norephedrine hydrochloride and 11 grams of paraformaldehyde were suspended in 400 ml of isopropanol and heated at boiling for 9 hours. A further 10 grams of paraformaldehyde were added within the reaction time in portions of 2 grams. The product crystallizing out upon cooling was filtered off with suction and recrystallized from ethanol/water. Yield: 48%, M.P. of the hydrochloride: 203°–204° C.

In a manner analogous to Example 1 the compounds

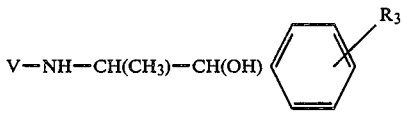

Examples (2–11) of Table 1 were obtained. The meanings of V and $R_3$ are set forth in column 1 of Table 1, NE=norephedrine.

TABLE 1

| | Product | | | | Starting Material | | |
|---|---|---|---|---|---|---|---|
| Example No. | V | $R_3$ | Melting Point of the Hydrochloride | Yield % | Amine Component Hydrochloride | Paraformaldehyde | Starting Ketone; Possible from Example 1 Variation |
| 2 | ![cyclohexene-CO-(CH2)2- with CH3] | H | 197 (Isopropanol) | 26 | 1-NE 11.2 g | 3.6 g | 9.5 g-2-Methyl-1-acetyl-1-cyclohexene |
| 3 | ![cyclopentene-CO-(CH2)2-] | H | 192 (Isopropanol) | 27 | 1-NE 63.8 g | 14 g | 47 g 1-Acetyl-1-cyclopentene |
| 4 | ![cycloheptene-CO-(CH2)2-] | H | 217–219 (Ethanol/H2O) | 40 | 1-NE 37.5 g | 7.5 g | 33.7 g 1-Acetyl-1-cycloheptene |
| 5 | ![cyclooctene-CO-(CH2)2-] | H | 199–200 (Ethanol/H2O) | 20 | 1-NE 18 g | 5 g | 14 g 1-Acetyl-1-cyclooctene |
| 6 | ![cyclohexene-CO-CH-CH2 with CH3] | H | 211–213 | 23 | 1-NE 43.2 g | 9 g | 39 g 1-Propionyl-1-cyclohexene |

TABLE 1-continued

| | Product | | | | Starting Material | | |
|---|---|---|---|---|---|---|---|
| Example No. | V | $R_3$ | Melting Point of the Hydrochloride | Yield % | Amine Component Hydrochloride | Paraformaldehyde | Starting Ketone; Possible from Example 1 Variation |
| 7 | Adamantyl-CO—$(CH_2)_2$ | H | 241 (Ethanol/Methanol) | 17 | 1-NE 9 g | 3 g | 9 g Acetyladamantane |
| 8 | Adamantyl-CO—$(CH_2)_2$ | 4-OH | 193–194 (Ethanol/Methanol) | 24 | dl-p-OH—NE 8 g | 2 g | 7 g Acetyladamantane |
| 9 | ▷—CO—$(CH_2)_2$— | H | 188 | 19 | 1-NE 18 g | 4 g | 9 g Acetylcyclopropane Reaction time 2–3 hours |
| 10 | cyclohexenyl-CO—$(CH_2)_2$— | 4-OH | 137–140 Oxalate (Isopropanol/Chloroform) | 15 | dl-p-OH—NE 10.25 g | 1.5 g | 6.2 g 1-Acetyl-1-cyclohexene solvent removed in vacuum; the base produced with $NH_3$ and the oxalate produced with isopropanolic oxalic acid solution, reaction time 6 hours |
| 11 | cyclohexyl-CO—$(CH_2)_2$— | H | 219–220 (Ethanol) | 15 | 1-NE 52 g | 12.6 g | 35 g Acetylcyclohexane Reaction time 2–3 hours |
| 12 | 2-chloro-cyclopentenyl-CO—$(CH_2)_2$ | H | 204–205° C. | 54 | 1-NE 13.1 g | 3 g | 10 g 1-Acetyl-2-chlor-1-cyclopentene |
| 13 | $(CH_2)_{10}$ with C=CH, C=O, $(CH_2)_2$ (cyclododecenyl) | H | 150–151° C. | 21 | 1-NE 18.8 g | 6 g | 20 g 1-Acetyl-1-cyclododecene |

EXAMPLE 14

1-[3-Hydroxy-3-phenyl-propyl-(2)]-(3-cyclohexyl-3-oxo-propyl)-amine 2.2 grams (0.01 mol) of (2-Dimethylamino-ethyl)-cyclohexylketone.HCl (produced by Mannich reaction from 1-acetyl-1-cyclohexene with formaldehyde and dimethylamine hydrochloride and subsequent hydrogenation with Pd-C as catalyst) and 1.5 grams (0.01 mol) of 1-norephedrine were dissolved in 20 ml of warm isopropanol. The product crystallizing out in the cooling was filtered off with suction and recrystallized from ethanol. Yield: 24%, M.P. of the hydrochloride 219°–221° C.

EXAMPLE 15

1-[3-Hydroxy-3-(4-hydroxyphenyl)-propyl-(2)]-(3-cyclohexyl-3-oxo-propyl)-amine

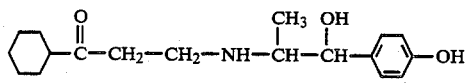

2.0 grams (0.009 mol) of (2-Dimethylamino-ethyl)-cyclohexylketone.HCl and 1.6 grams (0.009 mol) of 1-p-Hydroxynorephedrine were dissolved in 20 ml of warm isopropanol. The product crystallizing out in the cooling was filtered off with suction and recrystallized from isopropanol.

Yield: 24%, M.P. of the hydrochloride: 212°–214° C.

EXAMPLE 16

1-[3-Hydroxy-3-phenyl-propyl-(2)]-(3-cyclohexyl-3-oxo-propyl)-amine

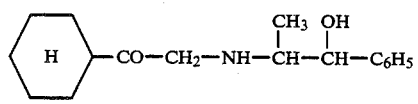

13.8 grams (0.1 mol) of cyclohexyl-vinylketone (obtainable by the splitting off of HCl during the distillation of cyclohexyl-β-chloroethyl ketone) and 15.1 grams (0.1 mol) of 1-norephedrine were dissolved in 50 ml of isopropanol. The desired compound crystallized out as the free base in the standing overnight. The production of the hydrochloride took place in the customary manner with isopropanolic hydrochloric acid. M.P. of the hydrochloride: 219°–221° C.

EXAMPLE 17

1-[3-Hydroxy-3-phenyl-propyl-(2)]-(3-cyclohexyl-3-oxo-propyl)-amine

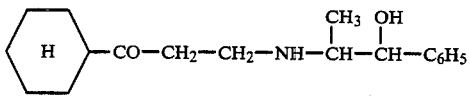

The oily cyclohexyl-β-chloroethyl ketone obtained from a solution of 200 grams (1.36 mol) of cyclohexanecarboxylic acid chloride in 500 ml of dried 1,2-dichloroethane by portionwise addition of 182 grams (1.3 mol) of AlCl$_3$ at −5° C., then leading ethylene through, subsequent hydrolysis with 500 ml of water at room temperature and concentration of the organic phase dried with Na$_2$SO$_4$ in a vacuum (analogous to U.S. Pat. No. 2,792,406) was added to a solution of 164 grams (1.09 mol) of 1-norephedrine in 1000 ml of dioxane. The desired product crystallized out overnight, was filtered off with suction and recrystallized from ethanol/water 1:1 (by volume). Yield: 67% (based on the cyclohexane carboxylic acid chloride). M.P. of the hydrochloride: 219°-221° C.

EXAMPLE 18

1-erythro-[3-Hydroxy-3-(3-hydroxyphenyl)-propyl]-(2)-(3-cyclohexyl-3-oxo-propyl)amine

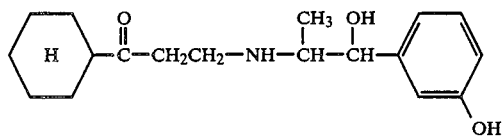

10 grams (0.057 mol) of cyclohexyl-β-chloroethyl ketone dissolved in 30 ml of acetonitrile at 75° C. were dropped into a mixture of 18 grams (0.057 mol) of 1-erythro-m-hydroxy-norephedrine hydrogen tartrate and 23.8 ml of triethylamine in 150 ml of acetonitrile. The mixture was heated for one hour at reflux, the solvent distilled off and the residue treated with 50 ml of hot water. After shaking three times with methyl isobutyl ketone there was added after drying with sodium sulfate the theoretically needed amount of oxalic acid (in 20 ml of methyl isobutyl ketone), needed to form the salt. The oxalate which crystallized out in the cooling was purified by recrystallization from isopropanol. Yield: 22%, M.P. of the oxalate: 174°-175° C.

EXAMPLE 19

1-threo-[3-Hydroxy-3-phenyl-propyl-(2)]-(3-cyclohexyl-3-oxo-propyl)-amine

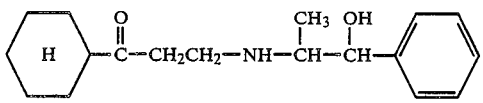

8.6 grams (0.057 mol) of 1-ψ-Norephedrine and 15.8 grams of potassium carbonate were heated in 150 ml of xylene with stirring to 100° C. and treated dropwise with a solution of 10 grams of cyclohexyl-β-(chloroethyl)-ketone in 30 ml of xylene. After the ending of the dropping in the mixture was heated a further hour under reflux and the solution filtered hot. The base crystallizing out in the cooling was dissolved in methyl ethyl ketone and treated with 10 ml of 5N isopropanolic hydrochloric acid. The hydrochloride obtained was recrystallized from isopropanol. Yield: 48%, M.P. of the hydrochloride: 172°-173° C.

EXAMPLE 20

1-[3-Hydroxy-3-phenyl-propyl-(2)]-(3-cyclohexyl-3-oxo-propyl)-amine.

There was dropped into a cyclohexyl magnesium bromide ether solution produced from 6.1 grams (0.25 mol) of magnesium and 48 grams (0.295 mol) of cyclohexyl bromide a solution of 25.2 grams (0.1 mol) of 1-2-norephedrine propionic acid ethyl ester in 150 ml of tetrahydrofuran at 5°-10° C. After heating for four hours under reflux the reaction mixture was poured on ice-salt (300 grams ice, 100 grams H$_2$O, 100 grams NH$_4$Cl) and the organic phase separated off. The aqueous phase was extracted several times with ether, dried over magnesium sulfate, the solvent distilled off in a vacuum and the hydrochloride produced with 8N isopropanolic HCl. This was recrystallized twice from ethanol/water (1:1 by volume). Yield: 6%, M.P. of the hydrochloride 219°-221° C.

EXAMPLE 21

1-[3-Hydroxy-3-phenyl-propyl-(2)]-(3-cyclohexyl-3-oxo-propyl)-amine

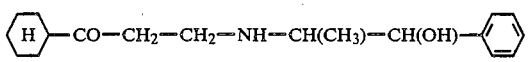

25 grams of 1-[3-Hydroxy-3-phenyl-propyl-(2)]-[3-(1-cyclohexene-1-yl)-3-oxo-propyl]-amine.HCl were dissolved in 250 ml of methanol/water (2:1 by volume), treated with 2.5 grams of Pd-C (10% palladium) and hydrogenated at 50° C. and 5 bar until the end of hydrogen take up. Then the catalyst was filtered off, the solvent distilled off in a vacuum and the product recrystallized from ethanol. Yield: 85% M.P. of the hydrochloride 219°-221° C.

Further example of the reduction step are entered in Table 2.

TABLE 2

| | Product of Formula I | | | | Melting Point (Hydrochloride) If Not Otherwise Noted | Yield | Amount of Starting Compound of Formula I added (as Hydrochloride). Only the residue is given, the remaining meanings are as in column 1 | Remarks |
|---|---|---|---|---|---|---|---|---|
| Ex. No. | R$_1$ | R$_2$ | R$_3$ | X | | | | |
| 22 | 2-Methyl-cyclohexyl | H | H | CO | 200° C. | 67% | R$_1$: 2-Methyl-1-cyclohexyl, 4 g | analogous to Example 21 |
| 23 | Cyclopentyl | H | H | CO | 194° C. | 62% | R$_1$: 1-Cyclopentenyl, 6.5 g | analogous to Example 21 |
| 24 | Cyclohexyl | CH$_3$ | H | CO | 211° C. | 60% | R$_1$: 1-Cyclohexenyl, 8 g | analogous to Example 21 |
| 25 | Cyclohexyl | H | 4-OH | CO | 160-161° C. | 59% | R$_1$: 1-Cyclohexenyl, 15 g | analogous to Example 21 from DL-p-OH—Norephedrine |
| 26 | Cyclohexyl | H | H | CHOH | 119° C. (Base) | 66% | X: CO, 10 g | * |
| 27 | 1-Cyclo- | H | H | CHOH | 212-213° C. | 68% | X: CO, 8 g | analogous to Example 26 |

TABLE 2-continued

| Ex. No. | Product of Formula I R₁ | R₂ | R₃ | X | Melting Point (Hydrochloride) If Not Otherwise Noted | Yield | Amount of Starting Compound of Formula I added (as Hydrochloride). Only the residue is given, the remaining meanings are as in column 1 | Remarks |
|---|---|---|---|---|---|---|---|---|
| 28 | hexenyl 1-cyclopentenyl | H | H | CHOH | 130–132° C. (Base) | 51% | X: CO, 10 g | analogous to Example 26 |
| 29 | Cycloheptyl | H | H | CO | 209–211° C. | 85% | R₁: 1-Cycloheptenyl 24.8 g | analogous to Example 21 |
| 30 | Cyclooctyl | H | H | CO | 190° C. | 81% | R₁: 1-Cyclooctenyl 6 g | analogous to Example 21 |
| 31 | Cyclododecyl | H | H | CO | 164° C. | 42% | R₁: 1-Cyclododecenyl 5 g | analogous to Example 21 |
| 32 | Cyclopentyl | H | H | CHOH | 197–198° C. | 52% | X = CO 5 g | analogous to Example 26 |
| 33 | Cyclohexyl | H | 4-OH | CHOH | 205° C. | 65% | X = CO (1-p-OH—NE) 2.2 g | analogous to Example 26 |
| 34 | Cyclo- | H | H | CHOH | 219–220° C. | 63% | X = CO 10 g | analogous to Example 26 |

*The starting material was dissolved in 100 ml of methanol and treated with a solution of 8 grams of sodium borohydride in 100 ml of methanol. The mixture was heated for 8 hours under reflux, treated with 50 ml of acetone and the solvent removed in a vacuum. After addition of 100 ml of water the mixture was extracted repeatedly with chloroform. The residue obtained after drying with sodium sulfate and subsequent removal of the solvent in a vacuum was crystallized from isopropanol.

EXAMPLE 35

(Production of the Free Base)

3 grams of 1-[3-Hydroxy-3-phenyl-propyl-(2)]-(3-adamantyl-3-oxo-propyl)-amine-hydrochloride were suspended in dilute ammonia. The suspension was shaken several times with chloroform. After drying and removal of the solvent in a vacuum the residue was recrystallized from isopropanol. Yield: 82%, M.P. 119°–121° C.

Examples of Pharmaceutical Preparations

EXAMPLE 36

| Tablets To make 100,000 tablets there were required | |
|---|---|
| 1. compound of Example 12 | 5.000 kg |
| 2. Magnesium stearate | 0.05 kg |
| 3. Lactose | 6.20 kg |
| 4. Microcrystalline cellulose | 6.70 kg |
| 5. Cornstarch | 1.00 kg |
| 6. Formalin treated casein | 1.00 kg |
| 7. Highly dispersed silica | 0.05 kg |
| Weight of the tablet nuclei: | 20.00 kg |

Production of the Tablets 1. 3.5 kg of microcrystalline cellulose were moistened with 0.4 liter of demineralized water.

2. The moistened microcrystalline cellulose was mixed with materials 2,5,6 and 7 in a suitable mixer for 5 minutes to produce Mixture 1.

3. Mixture 1 as well as materials 1 and 3 and the remainder of the microcrystalline cellulose were sieved (sieve having a mesh width of 0.8–1 mm) and homogeneously mixed in a suitable mixer to produce Mixture 2 also called "Molding Composition".

4. The relative humidity of the Molding Composition must be in the range of 40–45%.

5. The Molding Composition was subsequently molded to curved tablets having the following characteristics on a rotary pelleting press:

| Weight: | 200 mg |
|---|---|
| Diameter: | 8 mm |
| Radius of curvature: | 8 mm |
| Hardness: | 5–7 kg (Monsanto hardness tester) |

| -continued | |
|---|---|
| Decomposition time in cold water: | Maximum 5 minutes |

EXAMPLE 37

Injection Solution

To prepare 100 liters of injection solution there were required:

| 1. Compound of Example 12 | 0.90 kg |
|---|---|
| 2. Ethanol (96%) | 10.00 kg |
| 3. 1,2-propylene glycol | 25.00 kg |
| 4. Water suitable for injection purposes, sufficient to make | 100 liters |

Production of the injection Solution

Production of the injection solution was brought into solution in a mixture of 2,3 and 60 liters of water suitable for injection purposes under stirring on the waterbath. After cooling of the solution to 20° C. the pH was measured and if necessary adjusted to 2±0.2 by addition of 1N HCl. Then the solution was brought to a total volume of 100 liters with water suitable for injection purposes. This is the Active Material Solution.

The active material solution was sterilely filtered, filled into colorless ampoule glasses of 2 ml and then sterilized for 20 minutes at 120° C.

1 Ampoule equals 2 ml of injection solution containing 18 mg of active material.

What is claimed is:

1. A compound of the formula

IX

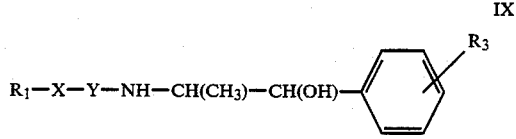

wherein X is the group >C=O or >CH(OH), Y is the group

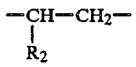

$R_2$ is hydrogen or $C_1$ to $C_6$ alkyl, $R_3$ is hydrogen or a hydroxy group, and $R_1$ is the adamantyl group or a saturated $C_3$ to $C_{16}$ cycloalkyl or single unsaturated $C_3$ to $C_{16}$ cycloalkenyl group where the cycloalkyl or cycloalkenyl group is unsubstituted or substituted by $C_1$ to $C_4$ alkyl or by halogen or a pharmaceutically acceptable salt thereof 2. A compound according to claim 1 wherein Y is

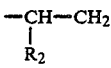

and $R_2$ is H or methyl and $R_1$ is adamantyl, $C_3$ to $C_{11}$ cycloalkyl with up to 1 methyl substituent or $C_3$ to $C_{11}$ cycloalkenyl with up to 1 methyl substituent.

3. A compound according to claim 1 wherein $R_2$ is hydrogen or $C_1$ to $C_4$ alkyl, and $R_1$ is adamantyl or $C_3$ to $C_{12}$ cycloalkyl or cycloalkenyl, the cycloalkyl or cyclokenyl having 0 to 2 substituents selected from the group consisting of methyl, ethyl, chlorine, bromine and fluorine.

4. A compound according to claim 3 wherein $R_1$ is adamantyl.

5. A compound according to claim 3 where $R_1$ is cycloalkyl, the cycloalkyl having 0 to 1 methyl or chlorine substituent.

6. A compound according to claim 3 where $R_1$ is cycloalkenyl, the cycloalkenyl having 0 to 1 methyl or chlorine substituent.

7. A compound according to claim 3 wherein $R_2$ is hydrogen or $C_1$ to $C_2$ alkyl and $R_1$ is adamantyl or $C_3$ to $C_8$ cycloalkyl or cycloalkenyl, the cycloalkyl or cycloalkenyl having 0 to 2 substituents selected from the group consisting of methyl, ethyl, chlorine, bromine and fluorine.

8. A compound according to claim 3 where $R_2$ is hydrogen or methyl.

9. A compound according to claim 8 where $R_2$ is hydrogen.

10. A compound according to claim 11 where $R_2$ is methyl.

11. A compound according to claim 8 where $R_1$ is adamantyl or cycloalkyl or cycloalkenyl having 0 to 1 methyl, ethyl, chlorine, bromine or fluorine substituent.

12. A compound according to claim 3 where X is $>C=O$.

13. A compound according to claim 3 where X is $>CH(OH)$.

14. A medicament containing as an active ingredient in an effective amount sufficient to increase blood flow of a mammal by dilating peripheral blood vessels a compound according to claim 1 together with a pharmaceutical excipient.

15. A method of increasing blood flow in a mammal by dilating peripheral blood vessels comprising administering to the mammal an amount of a compound of claim 1 effective for said purpose.

16. A method according to claim 15 wherein the compound is administered orally.

17. A method according to claim 16 wherein the compound is administered orally at least 0.3 mg/kg body weight of the mammal.

18. A method according to claim 15 wherein the compound is administered intravenously.

19. A method according to claim 18 wherein the compound is administered intravenously at least 0.1 mg/kg body weight of the mammal.

* * * * *